United States Patent
Mayer et al.

(10) Patent No.: US 11,504,320 B2
(45) Date of Patent: Nov. 22, 2022

(54) USE OF NATURALLY GLYCOSYLATED POLYPHENOLS AS PROTECTIVE AGENTS AGAINST THE EFFECTS OF ULTRAVIOLET IRRADIATION

(71) Applicant: MEDENA AG, Affoltern a. Albis (CH)

(72) Inventors: Wolfgang Mayer, Zürich (CH); Liudmila Korkina, Rome (IT)

(73) Assignee: Medena AG, Affoltern (CH)

( * ) Notice: Subject to any disclaimer, the term of this patent is extended or adjusted under 35 U.S.C. 154(b) by 0 days.

(21) Appl. No.: 16/613,858

(22) PCT Filed: May 18, 2017

(86) PCT No.: PCT/CH2017/000048
§ 371 (c)(1),
(2) Date: Nov. 15, 2019

(87) PCT Pub. No.: WO2018/209449
PCT Pub. Date: Nov. 22, 2018

(65) Prior Publication Data
US 2020/0146962 A1    May 14, 2020

(51) Int. Cl.
| | | |
|---|---|---|
| *A61K 8/60* | (2006.01) | |
| *A61K 8/04* | (2006.01) | |
| *A61K 8/27* | (2006.01) | |
| *A61K 8/29* | (2006.01) | |
| *A61K 45/06* | (2006.01) | |
| *A61Q 19/08* | (2006.01) | |

(52) U.S. Cl.
CPC ............... *A61K 8/60* (2013.01); *A61K 8/042* (2013.01); *A61K 8/27* (2013.01); *A61K 8/29* (2013.01); *A61K 45/06* (2013.01); *A61Q 19/08* (2013.01)

(58) Field of Classification Search
CPC . A61K 8/60; A61K 8/042; A61K 8/27; A61K 8/29; A61K 8/602; A61K 45/06; A61Q 19/08; A61Q 17/04
See application file for complete search history.

(56) References Cited

U.S. PATENT DOCUMENTS

| | | | |
|---|---|---|---|
| 5,565,435 A | 10/1996 | Yoneyama et al. | |
| 2007/0015262 A1 | 1/2007 | Dal Monte et al. | |
| 2008/0118463 A1* | 5/2008 | Pomytkin | ................. A61P 1/00 424/85.2 |
| 2008/0138439 A1* | 6/2008 | Soloviev | ................. A61K 8/19 424/613 |
| 2011/0123646 A1 | 5/2011 | Dal Monte et al. | |

FOREIGN PATENT DOCUMENTS

| | | | | |
|---|---|---|---|---|
| CA | 2644045 A1 * | 9/2007 | ............ | A61K 8/498 |
| CN | 102727411 B | 5/2014 | | |
| CN | 106109307 A | 11/2016 | | |
| EP | 2257266 B1 * | 3/2016 | ............... | A61K 8/35 |
| EP | 2257266 B1 | 3/2016 | | |
| JP | 2000319154 A | 11/2000 | | |
| KR | 20130049040 A * | 5/2013 | | |
| NZ | 264108 A | 5/1997 | | |
| WO | 03097577 A1 | 11/2003 | | |
| WO | WO-2006114189 A1 * | 11/2006 | ............ | A61Q 19/08 |
| WO | 2016113659 A1 | 7/2016 | | |

OTHER PUBLICATIONS

International Search Report dated Oct. 5, 2017 filed in PCT/CH2017/000048.

* cited by examiner

*Primary Examiner* — Ali Soroush
(74) *Attorney, Agent, or Firm* — Rankin, Hill & Clark LLP

(57) ABSTRACT

Use of a naturally glycosylated polyphenol, not containing nitrogen, as protective agent against the effects of ultraviolet irradiation on photo-degradable substances of structures.

15 Claims, No Drawings

USE OF NATURALLY GLYCOSYLATED POLYPHENOLS AS PROTECTIVE AGENTS AGAINST THE EFFECTS OF ULTRAVIOLET IRRADIATION

BACKGROUND OF THE INVENTION

1. Field of the Invention

The invention relates to the use of a naturally glycosylated polyphenol not containing nitrogen according to the preamble of claim 1.

2. Description of the Related Art

From WO 03/097577 SYNTH'E163 nitrogen-containing substances are known for protecting a sensitive material against UV radiation.

Higher plants and lower eucariots, such as marine micro/macroalgae, corals, jelly-fish, etc. synthesise primary metabolites essential for their growth, division, and propagation (proteins and aminoacids, lipids and fatty acids, poly- and oligosaccharides). They account for more than 90-95% of a dry weight of terrestrial and marine organisms. There are also secondary metabolites, which do not participate directly in the above described major functions of plants/marine organisms but are essential for signal transduction, for co-ordination of cell functions, and for defence and adaptation to continuously changing environmental conditions (to co-called biotic and abiotic stresses). For example, secondary metabolism in plants/marine organisms starts upon exposure to UV, X-ray or ultrasonic irradiation, temperature changes (cold or heat), heavy metal, salt, and organic toxin contents, mechanical damage, etc. It is also initiated by bacterial, viral or parasite infections, or by damage produced by herbivores and insects. In general, secondary metabolites are known as protective, adaptive, and regulatory (hormone-like) substances. It is believed that secondary metabolites play role of primitive "immune system" and "detoxification network" in plants and lower marine organisms.

All known so far secondary metabolites (more than 5,000 different substances) could be divided into three major classes in accord with their chemical structure:

phenyipropanoids (or ethylpropanoids) and their derivatives, such as simple polyphenolics (acids, alcohols, and aldehydes), aromatic polyphenols (bioflavonoids, stilbene, curcuminoids, coumarins, etc.), and glycosides. They contain carbon, hydrogen, and oxygen atoms and form aromatic or polyaromatic structures containing multiple hydroxyl groups and glycoside moieties, mainly, rhamnose, mannose, rutinose, etc.

terpenoids containing long mainly unsaturated C—H chain and nucleus of C—H non aromatic cycle nitrogen-containing heterocycles, such as alkaloids, purines, pirimidines, porphyrins, chlorophills, flavins, etc.

A great majority of secondary metabolites can interact somehow with solar UV irradiation:

some of them (for example, phenyipropanoids and their glycosides as well as bioflavonoids) are specialised exclusively ON the protection of biological structures from damaging effects of UV and visible light (photoreactions type I);

some of them (flavonoids, phenyipropanoids, and terpenoids) preferably protect cells and tissues against damaging effects of reactive oxygen species (superoxide anion-radicals, hydroxyl radicals, peroxides, and singlet oxygen) formed upon UV reaction with organic matter in the presence of molecular oxygen (photoreactions type II);

some of them (nitrogen-containing heterocycles and terpenoids) use energy of UV, visible or infra-red irradiation to promote biologically important photochemoreactions, such as photosynthesis or haemoglobin or terpenoid-containing polymer synthesis. They are called photosensitises.

These nitrogen-containing photosensitises (porphyrins, dihydropiridines, amino acid tryptophan and derivatives, retinoid acid, purines and pyrimidines) are widely present in different cells and tissues, first of all, in human skin cells. In FIG. 1 the process of interaction of solar light (quantum of light, UV, visible or infrared) with chromophores (CH) in the skin is schematically represented. A CH transforms into its excited state (CH*) with higher-than-initial energy.

An excited state is a short living one and transits into ground state with lower energy emitting energy in the form of heat, fluorescence or phosphorescence depending on electron structure of the molecule, its conjugated aromatic "π" electrons and 3D configuration of the entire molecule (the absence or presence of planar or perpendicular position of aromatic moieties as well as the presence of glycoside moiety). These molecules belong to sunscreens because they effectively scavenge solar light without initiation of any photochemical reaction. These molecules are usually photo-stable because they do not transform in photochemical derivate and they are not easily destroyed by solar irradiation. In human skin, these are melanin (pheomelanin), amino acid tyrosine and its derivatives. On the other hand, they can be also effective scavengers of reactive oxygen species formed upon type II photochemical reactions initiated by solar light.

In U.S. Pat. No. 5,565,435 YONEYAMA et al., a synthetically prepared glycosylated polyphenol alpha-glycosyl quercetin is proposed for cosmetic preparations as a skin-protecting agent. The proposal is based on an assumption that natural aglycon quercetin and its synthetic derivative alpha-glycosyl quercetin have absorption spectra with 2 maximums in UV area. No specific data has been presented to support their assumption.

BRIEF SUMMARY OF THE INVENTION

It is an object of the invention to provide naturally glycosylated polyaromatic polyphenols (GPPs) derived from medicinal plants for use as non-phototoxic active substances for physical, chemical, and biological protection of human skin from UV irradiation. Due to the particular chemical structure consisting of a polyaromatic polyphenolic moiety and a sugar moiety, GPPs absorb efficiently both UVB light (280-320 nm) and UVA light (320-400 nm) providing efficient physical/chemical screen from a broad spectrum UV irradiation. The presence of the sugar moiety provides their increased stability to UVA irradiation thus assuring long lasting photo-protection hence they are photo-stable molecules and are not destroyed by UVA light unlike the majority of synthetic sun screens. Being effective anti-oxidants, GPPs prevent reactive oxygen species-driven photochemical reactions hence preventing type II photo toxicity against skin cells and extracellular matrix. Possessing anti-inflammatory properties, GPPs block UV-induced cutaneous inflammation.

We are proposing here plant/plant cells/marine organisms-derived secondary metabolites belonging to the class of glycosylated phenyipropanoids/bioflavonoids possessing broad-band photo protective properties by the above mechanism of interaction of solar light with photo-stable and not photo-toxic protector with sunscreen and free radical scavenging properties.

At the same time, CH* could be a photosensitiser (PS), which transfer its excessive energy to initiate a photochemical reaction either directly with biologically active molecules thus inducing free-radical-driven damage to DNA, polysaccharides, and proteins (type I) or to molecular oxygen, which transforms from triplet into singlet (excited) state (type II). Reactive oxygen species formed under type II photo-induced reaction could be used for synthetic processes but mainly, they are harmful due to damaging potential to proteins, DNA, polysaccharides, and lipids. Nitrogen-containing plant- or marine-organism-derived substances are potentially dangerous because they can be chemo-photo-toxic, could induce photo-allergy, increase skin sensitivity, induce inflammation, redness, and itching. These substances could be however useful for photodynamic therapies of skin tumours, chronic inflammatory skin diseases, chronic melanisation defects, and skin infections.

The invention solves the posed problem with the use of naturally glycosylated polyphenols comprising the features of claim 1.

From a kinetic chemistry point of view, non nitrogen-containing phenylpropanoid or polyphenolic compounds should have a rather high activation energy and therefore would need UV irradiation to acquire an excited state. Due to their highly conjugated aromatic moieties with stable "π" configuration, their excited state lives longer and energy dissipates within the space of this particular molecule. Their aromatic rings are mainly in perpendicular positions that favours electron "entrap" within the molecule. An addition of glycoside moiety makes a configuration even more complicated for a possibility of electron escape.

For the invention as claimed data are presented in support of the surprising finding that definite naturally glycosylated polyphenols provide optimal photo-protection due to several reasons. They effectively absorb broad-band range of UV light in both spectrum regions: UVA and UVB. Their efficacy to absorb UVA+UVB is comparable to the golden standard of synthetic sunscreens (e.g. benzophenone-3). The efficacy of absorption is expressed as SPF (sun protection factor) for UVB range representing an integral of absorption within the whole UVB spectrum. The efficacy of absorption is also calculated as the UVA/UVB ratio showing that the ratio should be greater than 0.5 up to 1.2 in order to provide proper UVA protection.

All polyaromatic molecules with condensed structures having π bonds (likewise alpha-glycosylated quercetin) have absorption spectrum with two peaks within UV spectrum range. But the integral square under the spectral peaks is very often of small value (narrow and high peaks or wide and low peaks) and does not correspond to the internationally accepted SPF and UVA/UVB values. Hence these substances could not be considered as effective and broadband UV screens. See the comparative data shown in table 1 below on catechins, morin, quercetin, and baicalein versus taxifolin, verbascoside, leontopodic acids, and resveratrol.

TABLE 1

(Broad band ultraviolet B and A absorption by glycosylated and non- glycosylated plant polyphenols)

| Sunscreens | SPF1(250 µM) | SPF2 (10%) | UVA/UVB |
|---|---|---|---|
| Glycosylated polyphenols | | | |
| Taxifolin | 6.38 ± 0.12 | 8.39 ± 0.14 | 0.46 |
| Rutin | 5.25 ± 0.13 | 3.44 ± 0.16 | 1.20 |
| Silibinin | 6.44 ± 0.14 | 5.34 ± 0.16 | 0.46 |
| Verbascoside | 8.25 ± 0.09 | 5.29 ± 0.09 | 0.59 |
| Leontopodic acids | 11.83 ± 0.12 | 6.79 ± 0.12 | 0.51 |
| Acacetin | 4.86 ± 0.22 | 6.85 ± 0.19 | 0.77 |
| Baicalein | 3.65 ± 0.12 | 5.41 ± 0.12 | 1.14 |
| Non-glycosylated polyphenols | | | |
| Morin | 2.63 ± 0.08 | 3.48 ± 0.12 | 1.70 |
| Epicatechin | 0.10 ± 0.02 | 0.14 ± 0.04 | 0.25 |
| Chrysin | 1.62 ± 0.07 | 2.55 ± 0.07 | 0.96 |

SPF—sun protection factor corresponding to UVB absorption calculated for micromolar (SPF1) and weight % (SPF2) concentrations of sunscreens.
UVA/UVB—the ratio of UVA to UVB absorption.

Most of the polyaromatic polyphenols are unstable to exposure to UV irradiation therefore they are subjected to photo-destruction within a short period of time (quercetin, resveratrol, kaempferol, etc.).

The polyphenols according to the invention have the following advantages over prior art (in particular over U.S. Pat. No. 5,565,435 YONEYAMA et al.:

Quercetin and its alpha-glycosylated derivative are photo-unstable and cannot protect human skin form UV damage without being re-applied after 1-10 min of exposure to sun. It means the existing patented molecule provide a short-term uncontrolled protection which does not correspond to claim of a certain photo-protection and expectations of a proper protection.

The selected naturally glycosylated polyphenols according to the invention provide protection for a long period of time due to their high photo-stability.

A great majority of polyaromatic polyphenols, particularly, synthetic ones exhibit definite photo-chemo-toxicity due to the induction of photo-chemo damage to skin cells (see Table 3). This is true for quercetin and its alpha-glycosylated derivative, resveratrol, chalcone and many others. The phenomenon of photo-chemo-toxicity depends of UV-induced destruction of the parent molecule and cyto-toxicity exerted by the formed metabolites.

The selected naturally glycosylated polyphenols according to the invention do not promote photo-chemical reactions thus do not exert any photo-cytotoxicity. They are much safer for human use.

Synthesized glycosyls with alpha-bond are not subjected to enzymatic metabolism by natural human enzymes beta-glycosidases. Therefore, they remain un-metabolised within human skin that highly increases risks of adverse skin reactions to xenobiotics.

The naturally glycosylated polyphenols according to the invention are substrates for beta-glycosidases and are normally metabolised and excreted through normal metabolic routs which are not related to any risk of adverse skin reactions. They are much more bioavailable and biocompatible while less toxicity.

Consequently the polyphenols according to the invention overcome the safety and efficacy drawbacks of synthetic photo-protectors known in prior art.

Moreover, the natural glycosylated polyphenols according to the invention with broad-band photo-protective properties are much less expensive than synthetic polyaromatic polyphenols since targeted glycosylation is a time- and money-consuming process often yielding an un-controlled This position makes them susceptible for the phase II metabolic enzymes, which transfer sulfate, methyl, or glucuronic acid residues to polyphenol molecules and excrete them from a living organism. Alpha glycosylation makes plant-derived molecules non-metabolised hence very toxic for humans.

Natural glycosylation in 3 and 4 positions during plant biosynthesis results in the production of highly photostable derivatives unlike their aglycones (quercetin, myricetin, kaempherol, resveratrol, and baicalein) which were easily destructed upon exposure to solar simulated UVB+UVA irradiation as can be seen in the following table 2.

TABLE 2

Effect of solar simulating UV irradiation of SPF values of sunscreens (photo stability of sunscreens)

| | UV (66% UVA и 33% UVB) J/cm$^2$ | | | | |
|---|---|---|---|---|---|
| Sunscreens | 0 | 0.15 | 0.45 | 3.0 | 6.0 |
| Glycosylated PPs | | | | | |
| Taxifolin | 6.38 ± 0.12 | N/D | N/D | 6.38 ± 0.12 | 6.39 ± 0.12 |
| Rutin | 5.25 ± 0.13 | N/D | N/D | 5.25 ± 0.13 | 5.25 ± 0.13 |
| Silibinin | 6.44 ± 0.14 | 6.41 ± 0.14 | 6.46 ± 0.14 | 6.45 ± 0.14 | 6.44 ± 0.14 |
| Verbascoside | 8.25 ± 0.09 | N/D | N/D | 8.23 ± 0.12 | 8.26 ± 0.10 |
| Baicalein | 3.68 ± 0.15 | 3.63 ± 0.12 | 3.62 ± 0.13 | 3.69 ± 0.12 | 3.79 ± 0.12 |
| Non-glycosylated PPs | | | | | |
| Ghalcone | 8.15 ± 0.14 | 3.49 ± 0.20** | 3.33 ± 0.20 | 3.09 ± 0.23 | 2.88 ± 0.24 |
| Chrysin | 1.62 ± 0.07 | 1.24 ± 0.20* | 1.32 ± 0.20 | 1.17 ± 0.10 | 1.17 ± 0.10 |
| Resveratrol | 11.98 ± 0.11 | 4.81 ± 0.20** | 4.25 ± 0.20 | 4.93 ± 0.16 | 4.63 ± 0.10 |
| Quercetin | 4.31 ± 0.10 | 3.95 ± 0.20* | 3.79 ± 0.20 | 3.48 ± 0.20 | 3.16 ± 0.20** |
| trans-Ferulic acid | 7.34 ± 0.18 | 5.34 ± 0.09** | 3.91 ± 0.11 | 3.61 ± 0.13 | 3.74 ± 0.17 | mixture of glycosides with random positions of sugar moieties. This can hamper antioxidant capacity of polyphenols if one or more OH— groups are substituted by sugar moieties; or this can hamper their natural metabolism in human cells in the case accessible to enzymatic cleavage beta-bonds are substituted by non-accessible to enzymatic cleavage alpha-bonds.

NATURALLY biosynthesised GPPs are the first ones to be induced in plants upon exposure to solar UV irradiation. All NATURALLY glycosylated O— derivatives of polyphenols have monosaccharide or disaccharide moieties in the position 3 or very rare in the position 4 (Avicularin (quercetin-3-O-α-L-arabinoturanoside) CTN-986 Guaijaverin (quercetin 3-O-arabinoside) Heliosin (quercetin 3-digalactoside) Hyperoside (quercetin 3-O-galactoside) Isoquercetin (quercetin 3-O-glucoside) Miquelianin (quercetin 3-O-glucuronide) Quercetin 3,4'-diglucoside Quercetin-3-sophorodide Quercitrin (quercetin 3-O-rhamnoside) Rutin (quercetin rutinoside) Reinutrin (quercetin-3-D-xyloside) Spiraeoside (quercetin 4'-O-glucoside) Taxillusin (galloylated 3-O-glucoside of quercetin) or phenylpropanoid glycosides (verbascoside—an ester formed with the phenylethanoid hydroxytyrosol, the phenylpropanoid caffeic acid and the sugar alpha-L-rhamnosyl-(3)-beta-D-glucopyranose. All polyphenolic groups are not involved; teupolioside—an ester and glycoside formed by the caffeic acid and 4,5-hydroxyphenylethanol bound to a beta-D-glucopyranoside, rham nose, and galactose) or glycosylated stilbenes (polydatin-resveratrol-3-O-beta-D-glucopyranoside).

Fifty μM sunscreen solutions placed in 3.5 cm Petri dishes were irradiated by 66% UVA+33% UVB for 1, 3, 20, and 40 min. Final doses of UV irradiation were 0.15, 0.45, 3.0, and 6.0 J/cm$^2$, respectively. * p<0.05 vs background SPF; ** p<0.01 vs background SPF.

Further advantageous embodiments of the invention can be commented as follows:

In a preferred embodiment the polyphenol is a polyaromatic polyphenol.

In a further embodiment the polyphenol does not contain an aldehyde structure. It has been surprisingly found that the presence of an aldehyde group in the polyphenol makes it more susceptible to photo-destruction due to a decreased energy of photo-excitation.

Preferably the phenol is a glycosylated phenylpropanoid or phenylathanoid. Naturally glycosylated phenylpropanoids are the first to be formed through phenylpropanoid pathway in plants, cultured plant cells or marine organisms upon their irradiation with UV light. Surprisingly it was found that they are the major natural photo-protectors. The metabolic pathways of phenylpropanoid/flavonoid synthesis followed by glycosylation are extremely complicated and obscure so far. Chemical synthesis does not result in natural content, positions, and conformations of glycoside moieties. Moreover, this synthesis is extremely costly and synthetic glycosides imitating natural molecules are commercially non-acceptable.

In a further embodiment the polyphenol is verbascoside or teupolioside.

Still in a further embodiment the polyphenol a glycosylated flavonoid, flavonol or flavonol.

In a further embodiment the polyphenol is rutin, baicalein, morin or taxifolin.

The polyphenol may also be a glycosylated stilbenoid, preferably a polydatin.

In a further embodiment the polyphenol is obtained from the extracts of terrestrial plants or sea plants or other sea organism. In another embodiment the polyphenol is obtained from the extracts of plant cell cultures.

In a further embodiment a mixture of several polyphenols is used. This has the advantage that it covers a broader spectrum of UV irradiation.

Preferably the sugar moiety of the glycosylated polyphenol is rhamnose, arabinose or mannose. These sugar moities have surprisingly shown better results than glucose or fructose.

Preferably the use according to the invention is for topical protection from broad-band ultraviolet irradiation. Alternatively the use can be for biological protection from solar UV irradiation.

In a further embodiment the use of the polyphenol is for ameliorating natural photo-protection-related antioxidant properties of the skin, in particular protection of skin surface liposoluble antioxidants from photo-degradation Preferably the polyphenol is used as a component in a sun-protective composition. The polyphenol may advantageously be a component of a topical cosmetic composition, preferably in form of a gel, spray, cream or lotion.

The polyphenol may be admixed to a topical cosmetic composition like gels, sprays, creams, and lotions with photo-protective claims to increase photo-stability of topically applied drugs such as corticosteroids, non-steroidal anti-inflammatory drugs (NSAIDs), antibiotics, and antiviral remedies Preferably the use according to the invention is for protecting against remote biological consequences of UV irradiation like redness, swelling, pain, and premature ageing of the skin.

The polyphenol is preferably admixed to conventional physical sun screens, preferably $TiO_2$ or ZnO to fortify UV protection and to attenuate the physical sun screens toxicity.

The polyphenol may purposefully be applied in a concentration of at least 5 μM, preferably at least 10 μM. The concentration may purposefully by at least 20 μM, preferably at least 40 μM, The polyphenol is applied purposefully in a concentration of at most 500 μM, preferably at most 100 μM. The concentration is purposefully at most 80 μM, preferably at most 50 μM, In a preferred embodiment the polyphenol further comprises light water, preferably with a content of less than 125 ppm of $^2H$.

In a further special embodiment the polyphenol further comprises water which contains:
a) at least 500 ppm of $^{18}O$ and at most 1100 ppm of $^{18}O$; and
b) at least 20 ppm of $^2H$ and at most 90 ppm of $^2H$.

A Method for the treatment or prophylaxis against aging of the skin caused by exposure to oxidation comprises application of an effective amount of a polyphenol as defined by the use according to the invention.

The method is preferably for protecting the skin from photoreactions. The method may also be for reducing or preventing damage to the skin by oxidative influences. The polyphenol may be applied in a concentration of at least 5 μM, preferably at least 10 μM. Purposefully the concentration is at least 20 μM, preferably at least 40 μM.

The polyphenol may be applied in a concentration of at most 500 μM, preferably at most 100 μM. The concentration is purposefully at most 80 μM, preferably at most 50 μM.

The isolated naturally glycosylated GPPs or/and GPPs in extracts in topical cosmetic compositions like gels, sprays, creams, and lotions with photo-protective properties can be used for photo-sensitive groups like toddlers, children, pregnant women, immunosuppressed people, and ageing people

DETAILED DESCRIPTION OF THE INVENTION

The following examples clarify the invention further in more detail.

Example 1: Broad-Band Sun Protection Gel (SPF-B >50 and UV-A/UV-B Ratio >1)

| COMPONENT | Weigth % |
|---|---|
| AQUA | 58.02 |
| BAICALEIN (glycosylated flavonoid) | 8.00 |
| TAXIFOLIN (glycosylated flavonoid) | 7.00 |
| EXTRACT OF *SCUTELLARIA BAICALENSIS* (content of glycosylated polyphenols >80%) | 6.00 |
| EXTRACT OF MILK THISTLE SEEDS (content of glycosylated polyphenols >90%) | 5.00 |
| Excipients to provide product viscosity and fluidity (e.g glycerin, cetylpyridinium chloride) | 15.03 |
| Salts and buffers for pH control (f.e. sodium chloride, sodium hydroxide, and potassium chloride) | 0.95 |

Example 2: Broad-Band Sun Protection Light Cream (in Particular for Pregnant Women): SPF-B >50 and the UV-A/UV-B Ratio >0.5<1)

| COMPONENT | Weight % |
|---|---|
| AQUA | 48.3597156 |
| EXTRACT OF *ROSMARINUS OFFICINALIS* (content of glycosylated polyphenols >90%) | 6.0000000 |
| LEONTOPODIC ACIDS (glycosylated polyphenols) | 5.2000000 |
| EXTRACT OF *LEONTOPODIUM ALPINUM* MERISTEM CELLS (content of glycosylated polyphenols >90%) | 5.0000000 |
| EXTRACT OF *SYRINGA VULGARIS* MERISTEM CELLS (content of glycosylated polyphenols >75%) | 4.5000000 |
| Excipients for skin nutrition (e.g. fatty acids, long chain alcohols, lipids, glycerin and its derivatives) | 26.1694016 |
| Excipients to maintain cream viscosity and fluidity (e.g, microcrystalline cellulose, cyclopentasiloxane, cellulose gum, acrylates) | 1.9500000 |

-continued

| COMPONENT | Weight % |
|---|---|
| Excipients to preserve product against oxidative and microbial decomposition (e.g. phenoxyethanol, retinyl palmitate, *ANOGEISSUS LEIOCARPUS* BARK EXTRACT, tocopherol, *COENOCHLORIS SIGNIENSIS* EXTRACT | 1.5918000 |
| Excipients for skin moisturising (e.g. sodium hyaluronate, sodium stearoyl glutamate, dimethicone, maltodextrin, soluble collagen) | 0.8020000 |
| Parfume | 0.29992440 |
| Salts and buffers for pH control (sodium chloride, benzoate, phosphate, and hydroxide, potassium sorbate) | 0.1280000 |

15

Example 3: Broad-Band Sun Protection Milk in Particular for Babies and Children) SPF-B >50 and the UV-A/UV-B Ratio >0.5<1.0

| COMPONENT | WEIGHT % |
|---|---|
| AQUA | 58.4755157 |
| VERBASCOSIDE (PHENYLPROPANOID DIGLYCOSIDE) | 6.5000000 |
| EXTRACT of *VERBENA OFFICINALIS* (CONTENT OF GLYCOSYLATED POLYPHENOLS >95%) | 6.0000000 |
| KAEMPFEROL MONOGLYCOSIDE | 5.0000000 |
| EXTRACT OF *SAMBUCUS NIGRA* (CONTENT OF GLYCOSYLATED POLYPHENOLS >92%) | 5.0000000 |
| Excipients to provide viscosity and fluidity (e.g. paraffin, dicapryryl carbonate, sodium polyacrylate, xanthan gum, lauryl glucoside | 12.0875000 |
| Excipients to provide solidity and smooth/even distribution on the skin surface (e.g. butters, lecithin, glycerin and its derivatives) | 5.6030000 |
| Excipients to preserve product from oxidation and microbial degradation (e.g. phenoxyethanol, disodium EDTA, tocopherol and tocopheryl acetate, ascorbyl palmitate) | 1.0120000 |
| Perfume | 0.2999843 |
| pH control (sodium hydroxide) | 0.0220000 |

Example 4: Broad-Band Sun Protection Spray (30<SPF-B<50 and the UV-A/UV-B Ratio >1)

| COMPONENT | WEIGHT % |
|---|---|
| EXTRACT OF OSAGE ORANGE (content of glycosylated polyphenols >90%) | 5.0000000 |
| EXTRACT OF MILK THISTLE SEEDS (content of glycosylated flavonoids >75%) | 5.0000000 |
| MORIN (glycosylated flavonoid) | 4.6000000 |
| EXTRACT OF *SOPHORA JAPONICA* FLOWERS (content of glycosylated flavonoid rutin >90%) | 3.5000000 |
| Excipient - solvent (distilled water) | 1.6070614 |
| Excipients - Organic solvents and gases (e.g. isobutane, alcohol denat., propane, butane) | 79.9201130 |
| Excipients to provide viscosity (e.g. PVP, isosteareth-20, PEG-12 dimethicone) | 0.3045000 |
| Excipients to prevent oxidative and microbial decomposition (e.g. panthenol, limonene, linalool) | 0.0381136 |
| Perfume | 0.0302120 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:

1. A method for protecting human skin from UV irradiation comprising applying a composition to the skin, wherein:
   the composition comprises a naturally glycosylated polyphenol not containing nitrogen selected from the group consisting of verbascoside, teupolioside, baicalein, silibin and leontopodic acid;
   the naturally glycosylated polyphenol is present in the composition at a concentration of at least 20 µM;
   the composition further comprises water which contains at least 500 ppm of $^{18}O$ and at most 1100 ppm of $^{18}O$, and
   at least 20 ppm of $^{2}H$ and at most 90 ppm of $^{2}H$.

2. The method according to claim 1, wherein the naturally glycosylated polyphenol is obtained from extracts of terrestrial plants, sea plants, sea organisms or plant cell cultures.

3. The method according to claim 1, wherein the composition comprises a mixture of two or more selected from the group.

4. The method according to claim 1, wherein a sugar moiety of the glycosylated polyphenol is rhamnose, arabinose or mannose.

5. The method according to claim 1, wherein the composition ameliorates natural photo-protection-related antioxidant properties of the skin.

6. The method according to claim 1, wherein the composition is a sun-protective composition.

7. The method according to claim 1, wherein the composition is a topical cosmetic composition in a form of a gel, spray, cream or lotion.

8. The method according to claim 1, wherein the composition further comprises one or more topically applied corticosteroids, non-steroidal anti-inflammatory drugs, antibiotics or anti-viral agents.

9. The method according to claim 1, wherein the composition protects skin against redness, swelling, pain or premature ageing of the skin.

10. The method according to claim 1, wherein the composition further comprises $TiO_2$ and/or $ZnO$.

11. A composition for topical application to human skin for treatment or prophylaxis against aging of the skin caused by exposure to oxidation, the composition comprising an effective amount of a naturally glycosylated polyphenol not containing nitrogen selected from the group consisting of verbascoside, teupolioside, baicalein, silibin and leontopodic acid, wherein the naturally glycosylated polyphenol is present in the composition at a concentration of at least 20 µM, and wherein the composition further comprises water which contains at least 500 ppm of $^{18}O$ and at most 1100 ppm of $^{18}O$ and at least 20 ppm of $^{2}H$ and at most 90 ppm of $^{2}H$.

12. The composition according to claim 11, wherein the naturally glycosylated polyphenol is present in the composition at a concentration of at most 500 µM.

13. The composition according to claim 11, wherein the naturally glycosylated polyphenol is present in the composition at a concentration of at most 80 µM.

14. The composition according to claim 11, wherein the composition further comprises $TiO_2$ and/or $ZnO$.

15. The composition according to claim 11, wherein the composition further comprises one or more topically applied corticosteroids, non-steroidal anti-inflammatory drugs, antibiotics or anti-viral agents.

* * * * *